(12) United States Patent
Guillermo et al.

(10) Patent No.: US 10,675,413 B2
(45) Date of Patent: Jun. 9, 2020

(54) DELIVERY DEVICE

(71) Applicant: SHL MEDICAL AG, Zug (CH)

(72) Inventors: Carlos Guillermo, Los Osos, CA (US); David Desalvo, Lake Hiawatha, NJ (US); Lucio Giambattista, East Hanover, NJ (US)

(73) Assignee: SHL MEDICAL AG, Zug (CH)

( * ) Notice: Subject to any disclaimer, the term of this patent is extended or adjusted under 35 U.S.C. 154(b) by 294 days.

(21) Appl. No.: 15/070,870

(22) Filed: Mar. 15, 2016

(65) Prior Publication Data

US 2016/0193417 A1 Jul. 7, 2016

Related U.S. Application Data

(63) Continuation of application No. 12/599,766, filed as application No. PCT/EP2008/055785 on May 9, 2008, now Pat. No. 9,878,103.

(30) Foreign Application Priority Data

May 23, 2007 (SE) ...................... 0701249

(51) Int. Cl.
*A61M 5/315* (2006.01)
*A61M 5/31* (2006.01)
(Continued)

(52) U.S. Cl.
CPC ...... *A61M 5/3158* (2013.01); *A61M 5/31528* (2013.01); *A61M 5/31553* (2013.01);
(Continued)

(58) Field of Classification Search
CPC ............ A61M 5/3158; A61M 5/31528; A61M 5/31553; A61M 5/31585
(Continued)

(56) References Cited

U.S. PATENT DOCUMENTS 4,592,745 A * 6/1986 Rex .......................... A61M 5/24
604/152
5,249,598 A * 10/1993 Schmidt ........... B60K 15/03519
137/493.1
(Continued)

FOREIGN PATENT DOCUMENTS

EP     1547694 A2     6/2005

OTHER PUBLICATIONS

International Search Report issued in PCT/EP2008/055785 dated Jul. 30, 2008.
(Continued)

*Primary Examiner* — Phillip A Gray
(74) *Attorney, Agent, or Firm* — McDonnell Boehnen Hulbert & Berghoff LLP

(57) ABSTRACT

The present invention relates to a delivery device for delivering predetermined amounts of fluid, comprising a body (10), a container (16) filled with fluid to be delivered arranged inside said body, said container comprising an opening for expelling said fluid and a wall (18) movable inside said container (16), a threaded plunger rod (46) arranged movable inside said body (10) in the longitudinal direction and in contact with said movable wall (18), a manually operated push means (14, 60) movable in the longitudinal direction capable of, upon operation, move said plunger rod (46) towards said movable wall (18), thereby expelling fluid, and means for transforming a generally linear movement of said push means (14, 60) to a rotational movement of said plunger rod (46).

24 Claims, 6 Drawing Sheets

Related U.S. Application Data

(60) Provisional application No. 60/917,728, filed on May 14, 2007.

(51) Int. Cl.
*A61M 5/32* (2006.01)
*A61M 39/22* (2006.01)

(52) U.S. Cl.
CPC ...... *A61M 5/31585* (2013.01); *A61M 5/3202* (2013.01); *A61M 39/22* (2013.01); *A61M 5/3146* (2013.01); *A61M 5/3156* (2013.01); *A61M 5/31571* (2013.01); *A61M 5/31595* (2013.01); *A61M 2005/3104* (2013.01); *A61M 2005/3128* (2013.01)

(58) Field of Classification Search
USPC .......................................................... 604/207
See application file for complete search history.

(56) References Cited

U.S. PATENT DOCUMENTS

| | | | | |
|---|---|---|---|---|
| 2002/0058908 A1* | 5/2002 | Zierenberg | ............... | A61M 5/30 604/72 |
| 2005/0139613 A1* | 6/2005 | Francavilla | ........... | G01F 11/025 222/321.7 |

OTHER PUBLICATIONS

Written Opinion of the International Searching Authority issued in PCT/EP2008/055785 dated Jul. 30, 2008.

\* cited by examiner

DELIVERY DEVICE

CROSS REFERENCE TO RELATED APPLICATIONS

The present application is a continuation of U.S. patent application Ser. No. 12/599,766 filed Nov. 11, 2009 which is a 371 of International Application No. PCT/EP2008/055785 filed May 9, 2008 which claims the benefit of U.S. Provisional Patent Application No. 60/917,728 filed May 14, 2007 and which claims the benefit of Swedish Patent Application No. 0701249-5 filed May 23, 2007 the entire contents of which are incorporated entirely herein by reference.

TECHNICAL FIELD

The present invention relates to a delivery device and in particular a medical delivery device.

BACKGROUND ART

There are numerous different types of delivery devices on the market and even more delivery devices that have been developed but have not reached any market. The devices display different degrees of automation and functions depending on the particular demands and requirements.

The delivery devices range from dispensers for cosmetic products to medical delivery devices for administering vital drugs, such as injectors, inhalers and nebulisers, where many are quite advanced. With the advanced functions comes the necessity for rather complex mechanical solutions requiring a large number of components that have to be able to interact with each other in a reliable and safe way, in particular when dealing with vital drugs.

This in turn means that the cost of the devices becomes rather high and there is further a risk that the advanced functions requires complex handling steps in order to operate the device for administering a drug dose. For a number of persons that use this type of device, the complexity may be too much, leading to improper handling of the device, which in turn could lead to serious consequences.

For some types of application, the device need not be so advanced or it could be that the cost of the device needs to be kept as low as possible, but still needs to have a decent functionality. Another aspect when dispensing of fluids is the tendency of drooling after a dose has been delivered. This is quite common for some types of delivery devices because of the "resiliency" of the system, such as residual tension in springs, in rubber stoppers inside cartridges and the like.

The document EP 1 547 694 deals with a dispenser solution where the focus is on low manufacturing and filling costs. It comprises an outer casing and a fluid insert where the fluid insert is moved between two positions for dispensing a dose. This solution is obviously very cost-effective but the handling functionality is not optimal. It has further no means for preventing drooling of fluid after delivered dose. There is thus a need for a cost-effective delivery device that also comprises a good functionality.

DISCLOSURE OF INVENTION

The aim of the present invention is to remedy the drawbacks of the state of the art devices described above.

This aim is solved by a delivery device according to the independent patent claim. Preferable embodiments are the subject of the dependent patent claims.

According to a main aspect of the invention it is characterised by a delivery device for delivering predetermined amounts of fluid, Delivery device for delivering predetermined amounts of fluid, comprising a body, a container filled with fluid to be delivered arranged inside said body, said container comprising an opening for expelling said fluid and a wall movable inside said container, a threaded plunger rod (46) arranged movable inside said body in the longitudinal direction and in contact with said movable wall, a manually operated push means movable in the longitudinal direction capable of, upon operation, move said plunger rod towards said movable wall, thereby expelling fluid, and means for transforming a generally linear movement of said push means to a rotational movement of said plunger rod, wherein said transforming means comprises a first set of surfaces arranged to said manually operated push means inclined with respect to the longitudinal direction co-acting with a second set of inclined surfaces arranged on a rotatable drive means rotatably locked to said plunger rod.

According to another aspect of the invention, said second set of inclined surfaces are arranged around the circumference of the drive means having a predetermined number of degrees to each other corresponding to the predetermined amount of fluid to be delivered.

According to a further aspect of the invention, said drive means is arranged with a ratchet interface co-operating with a fixed ratchet interface arranged on the body for preventing a return movement of said drive means.

According to yet an aspect of the invention, the device further comprises means capable of unlocking said push means between a position where said push means are locked from being manually operated in the longitudinal direction to a position enabling operation.

According to another important aspect, the device further comprises a dose delivery means attached to the opening of said container wherein a closing valve is arranged to open above a certain pressure inside said container and to close below said pressure.

The present invention displays a number of advantages. The use of a push means that is manually operable in a linear manner is easy and convenient for the user to handle at the same time as a rotational movement for applying pressure to a fluid for expelling it means a better utility of the manual force from the user, because for many fluids a linear manual force is too low for expelling a fluid through an opening in the container. This is especially the case for fluids with high viscosity.

Preferably the transformation from linear movement to rotational movement is performed with inclined surfaces such as ramps and ratchet interfaces which are simple and cost-effective to manufacture with few components.

By varying the inclination of the ramps and the pitch of the threads it is possible to adjust the quantity of the delivered dose and to set the force required to deliver said dose in a simple and effective way.

Preferably the device is arranged with a valve at the delivery opening for preventing drooling at the end of delivered dose. Because the valve preferably is opened and closed by the pressure from the delivered fluid a reliable opening and closing of the valve is obtained at start and end of dose delivery.

The device could also be arranged with dose delivering units such as injection needles, aerosol nozzles and nebulising nozzles for different types of application, drug containers and use.

These and other aspects of and advantages with the present invention will become apparent from the following detailed description and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
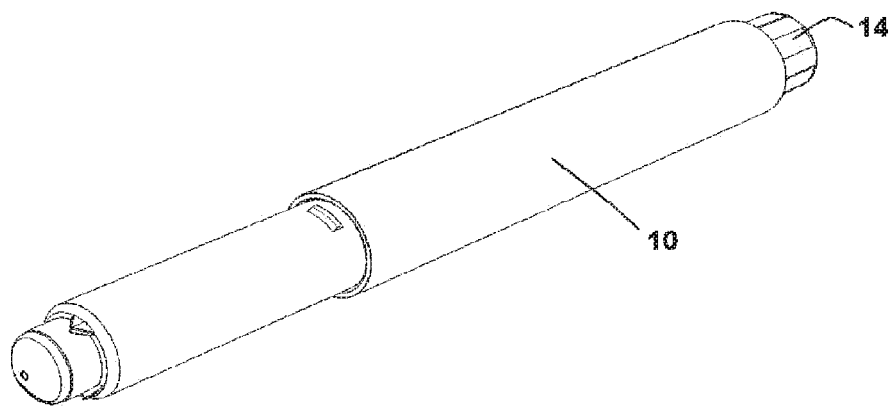
FIG. 1 is a perspective view of one embodiment of the present invention.
Figure 2:
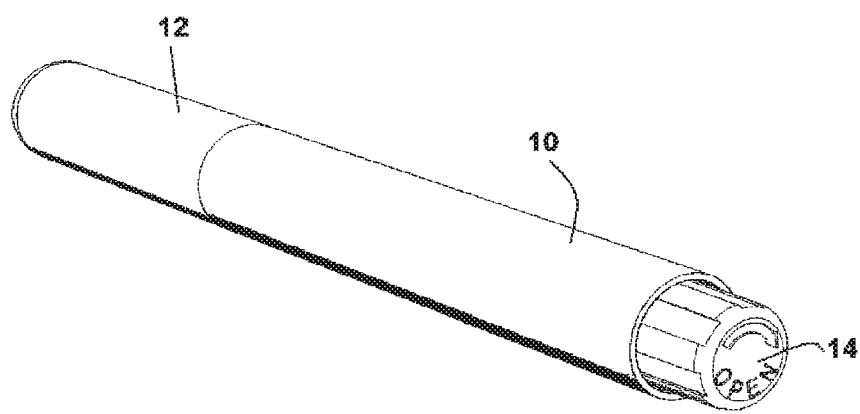
FIG. 2 is another perspective view of the embodiment of FIG. 1.

The device according to the present invention is shown in the drawings. The device comprises an elongated body 10 having a front end and a rear end, FIGS. 1 and 2. The front end is in the storage and pre-use state arranged with a removable cap 12. The rear end is arranged with a protruding button 14, hereafter named thumb button, the function of which will be described below.

Figure 3:
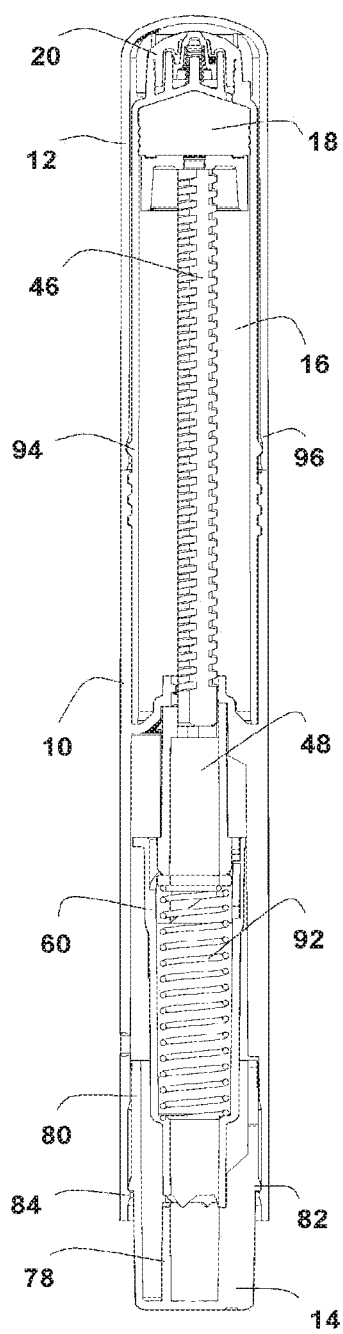
FIG. 3 is a cross-sectional side view of one embodiment of the present invention.
Figure 7:
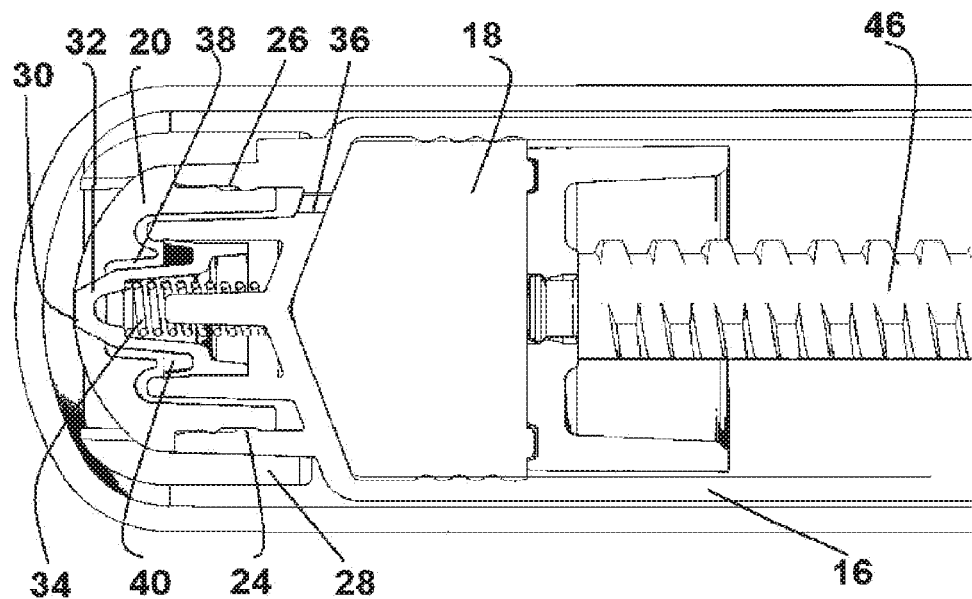
FIG. 7 is a detailed view in cross-section of the front part of the embodiment of FIG. 1.

As seen in FIG. 3 a container 16; e.g. a cartridge, a syringe, a cream container, a gas container; comprising fluid to be delivered is inside the body. A movable wall 18 is arranged inside the container. At the front end of the container an end piece 20 is attached, for example by a cylindrical part 22 having outwardly directed grooves and/or protrusions 24 mating with inwardly directed grooves and/or protrusions 26 of a cylindrical part 28 of the container. FIG. 7.

The end piece is arranged with a central opening 30, through which the fluid may be expelled. A valve 32 is arranged in the vicinity of the central opening, arranged with a front part having a shape corresponding to the central opening. A valve resilient means 34, e.g. a spring, arranged between the valve and the container urges the valve into the central opening. A passage 36 is arranged between the interior of the container and a space 38 between the valve and the end piece, delimited by an annular surface 40 of the valve on the opposite side of the valve resilient means.

Figure 8:
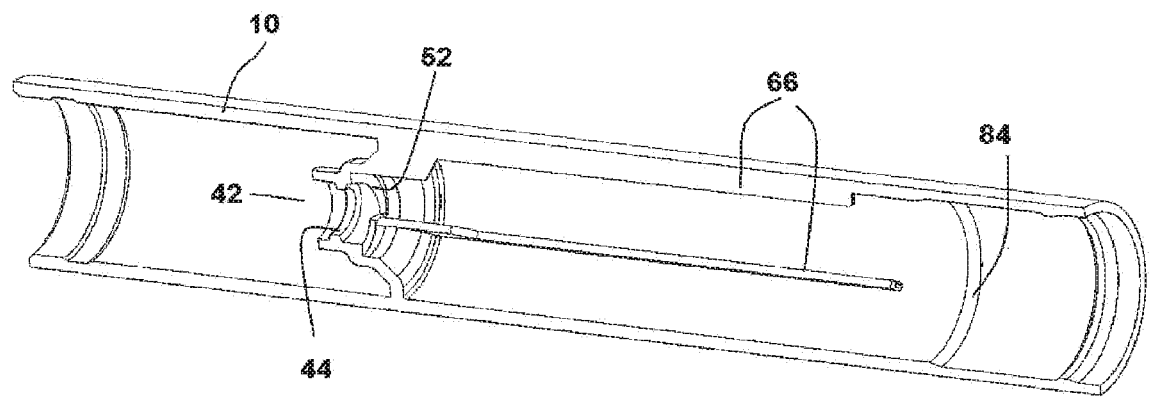
FIG. 8 is a view in cross-section of a component comprised in the embodiment of FIG. 1.
Figure 10:
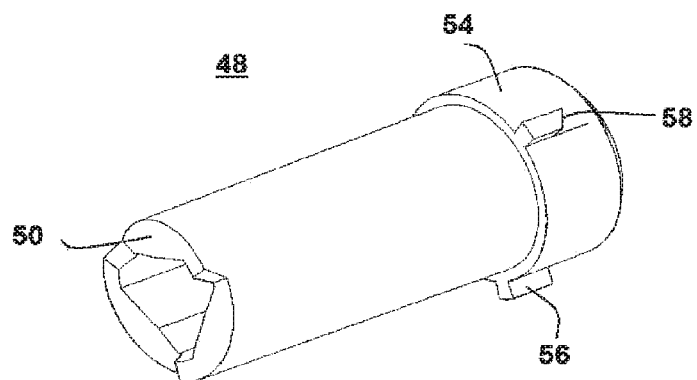
FIG. 10 is a perspective view of a further component.

The body 10 is further arranged with a central passage 42 arranged with threads 44 and ramps 52, FIG. 8, through which a threaded plunger rod 46 is arranged. A generally cylindrical part, hereafter named driver 48, FIG. 10, is arranged adjacent the threaded passage. The plunger rod extends through the driver in a rotationally locked, but slidable manner with the help of a spline design. The front end surface of the driver is arranged with a ratchet interface having inclined ramps 50 co-acting with a surface surrounding the central passage with corresponding ramps 52 of the body 10, FIG. 8, the function of which will be described below. A rear end 54 of the driver has a somewhat larger diameter and is arranged with a number of outwardly directed protrusions 56 on its circumference, where the rearwardly directed surfaces 58 are somewhat inclined. In the shown embodiment there are three protrusions arranged 120° to each other around the circumference.

Figure 11A:
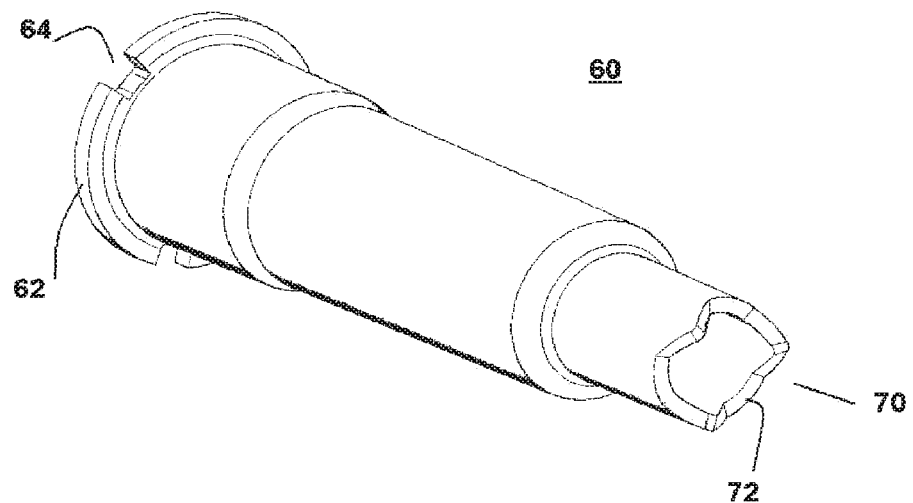
FIGS. 11a and 11b are perspective views of yet a component of the embodiment.
Figure 11B:
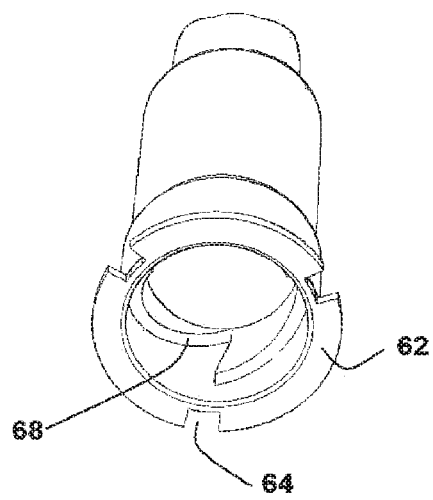

The driver 48 is co-acting with a further generally cylindrical part, hereafter named toggle sleeve 60, FIGS. 11a and b. The front end of the toggle sleeve is arranged with a circumferential ledge 62 having a number of cut-outs 64, which mate with longitudinal ridges 66 on the inner surface of the body 10, FIG. 8. At the inner walls of the toggle sleeve inclined ridges 68 are arranged, which cooperate with the inclined surfaces 58 of the protrusions 56 of the driver 48 in a manner that will be explained.

Figure 9:
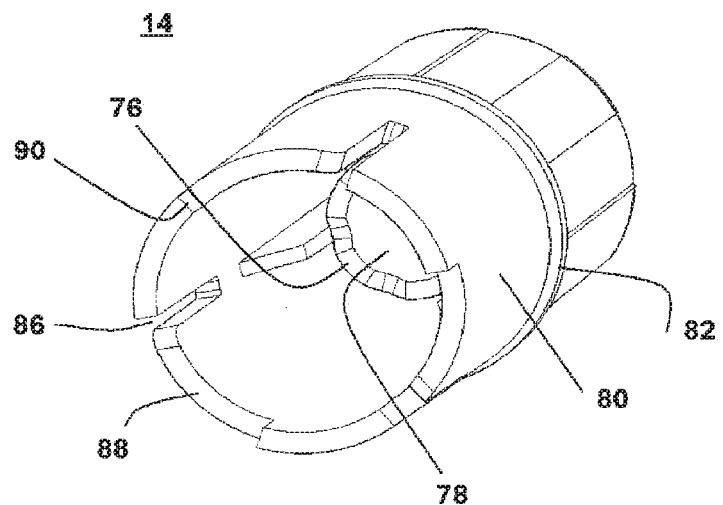
FIG. 9 is a perspective view of another component of the embodiment.

The rear end surface 70 of the toggle sleeve 60 is arranged with inclined surfaces 72, which surfaces co-act with corresponding surfaces 76 of a tubular part 78 of the thumb button 14, FIG. 9. The thumb button is arranged with a front cylindrical part 80 inside the body and is prevented from moving rearwardly by a circumferential ledge 82 in contact with an inwardly directed ledge 84 of the body 10. The front cylindrical part of the thumb button is further arranged with longitudinal grooves 86 arranged with a pitch and a width corresponding to the longitudinal ridges 66 of the body 10. In a first embodiment, the front end surface of the thumb button, shown in FIG. 9, is arranged with a number of inclined surfaces 88 and stop ledges 90. In a second embodiment, the perimeter surface of the thumb button is further arranged with a release button as e.g. a bump, not shown, which is capable of interact with a respective through hole or indentation, not shown, on the perimeter surface of the body 10 at its rear end. Moreover, a resilient means 92, e.g. a spring, is arranged between an inner surface of the thumb button and the rear end of the driver.

Figure 4:
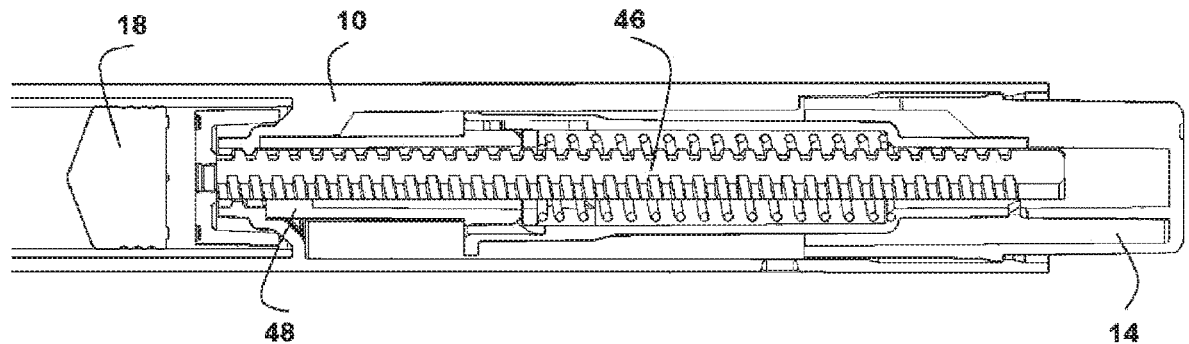
FIGS. 4 to 6 are detailed views in cross-section of the rear part of the embodiment of FIG. 1.
Figure 5:
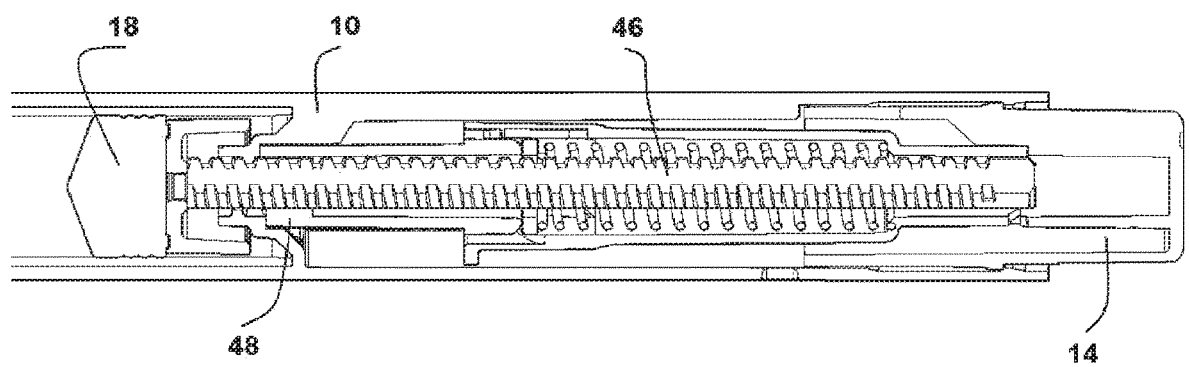

The device is intended to function as follows. When the device is delivered to the user, the end cap 12 is on and held in place by an annular ledge 94 on the outer surface of the container cooperating with an annular groove 96 on the inner surface of the cap. The cap is removed by pulling it off the device. The thumb button is in the locked position, FIG. 4. The next step is to enable delivery of fluid. In the first embodiment, the thumb button 14 is unlocked by being turned until the stop ledges 90 on the front end surface come in contact with the ridges 66 of the body. In the second embodiment, the thumb button 14 is unlocked by pressing the release button whereby the thumb button is ejected towards its rear end and forced to turn until the stop ledges 90 on the front end surface come in contact with the ridges 66 of the body due to the pressure exerted by the spring 92. The inclined surfaces 72 of the toggle sleeve 60 and the mating surfaces 76 of the thumb button 14 serve the purpose of holding the thumb button in the "closed" and "open" positions as well as providing tactile feedback to the user. In the open position the ridges 66 are aligned with the grooves 86 of the thumb button, thereby enabling the thumb button to be pushed into the body, i.e. enabling use of the device for delivery of fluid, FIG. 5.

Figure 6:
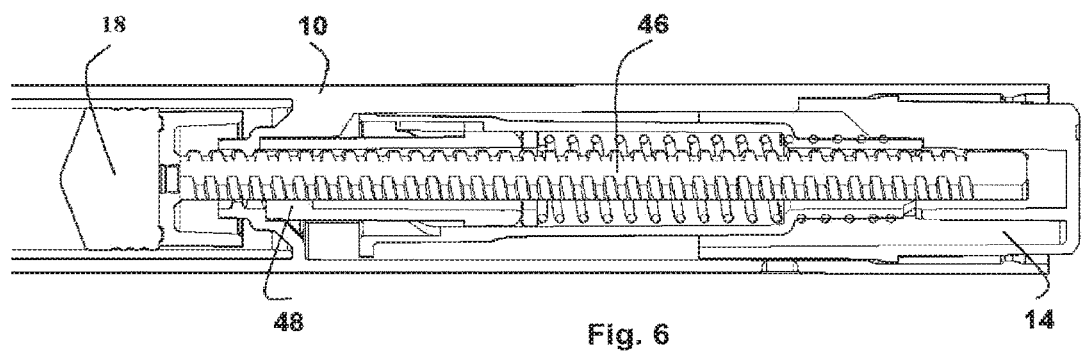

The pressing of the thumb button causes the toggle sleeve 60 to move forward, FIG. 6. This in turn will cause the driver 48 to rotate because of the inclined ridges 68 of the toggle sleeve acting on the end surfaces 58 of the protrusions 56 of the driver. The rotation of the driver is transmitted to the plunger rod 46 because of the rotational lock between them, and due to the threads of the plunger rod cooperating with the threads of the body; the plunger rod will move forward and thus press the movable wall 18 towards the front end of the device.

The pressure from the movable wall will press the fluid through the passage 36 in the end part of the container and then act on the annular surface 40 of the valve 32. This pressure will cause the valve to open against the force of the valve resilient means 34, thereby expelling the fluid through the central opening 30. As soon as the pressure from the fluid decreases below the force of the valve resilient means, the valve will close, thereby preventing any drooling of the fluid.

When the driver has rotated about 120° the ratchet interface between the driver and the body is such that the ramps 50, 52 falls into the next indexed position and the dose is completed. The ramps providing the indexed positions prevent any backdriving of the driver. When the user releases the pressure on the thumb button, the force from the resilient means 92 will force the toggle sleeve back to its original position in the longitudinal direction. In order for the inclined ridges 68 of the toggle sleeve to be able to act on the protrusions 56 of the driver for subsequent delivery, the toggle sleeve has to be slightly rotated which is done with the ramps 72 on the rear end of the toggle sleeve working with the mating ramps 76 on the thumb button. In that respect the cut-outs 64 on the toggle sleeve are made somewhat wider than the ridges 66 of the body to permit this slightly rotation.

Preferably the device is primed before the first use. This is done by holding the device with the front end pointing upwards and by pressing the thumb button a number of times.

It is to be understood that the device can be modified in many ways. Even though a rotation of 120° has been described, other pitches may be chosen depending on for example the dose quantity. In that respect the number of degrees to each other of the second set of inclined surfaces arranged around the circumference of the drive means may be modified and the pitch of the threads may also be modified to provide different lengths that the plunger rod is moved, thus providing different dose quantities.

It is further to be understood that the device may be provided with different delivery means such as injection needles attached to the front end of the container for enabling injection of fluid, spray nozzles when the device is to be used as inhaler or nebuliser.

In this respect it is to be understood that the embodiment described above and shown in the drawings is to be regarded only as non-limiting example of the invention and that it may be modified in many ways within the scope of protection by the patent claims.

The invention claimed is:

1. A delivery device, comprising:
an elongated body comprising a front end and a rear end;
a button arranged within the rear end of the elongated body;
a non-rotating, axial moveable sleeve, wherein the sleeve comprises a front end and a rear end, wherein the rear end of the sleeve is configured to interact with the button;
a rotatable cylindrical driver comprising a front end and a rear end, wherein the rear end of the rotatable cylindrical driver is configured to directly interact with the front end of the non-rotating, axial moveable sleeve; and
a rotating threaded plunger rod extending through the rotatable cylindrical driver.

2. The delivery device according to claim 1, wherein the rotatable cylindrical driver is not axially moveable.

3. The delivery device according to claim 1, wherein the elongated body comprises a passage arranged with threads through which the rotating threaded plunger rod is arranged.

4. The delivery device according to claim 3, wherein the front end of the rotatable cylindrical driver is arranged adjacent the passage of the elongated body.

5. The delivery device according to claim 1, wherein the rotating threaded plunger rod extends through the rotatable cylindrical driver in a rotationally locked, but slidable manner.

6. The delivery device according to claim 5, wherein the rotating threaded plunger rod extends through the rotatable cylindrical driver in a rotationally locked, but slidable manner by way of a spline design.

7. The delivery device according to claim 3, wherein a front end surface of the front end of the rotatable cylindrical driver comprises a ratchet interface comprising inclined ramps arranged to co-act with corresponding ramps provided on a surface surrounding the passage of the elongated body.

8. The delivery device according to claim 1, wherein the front end of the sleeve comprises a circumferential ledge, the circumferential ledge comprising a plurality of cut-outs,
wherein the cut-outs are configured to mate with a plurality of longitudinal ridges provided along an inner surface of the elongated body.

9. The delivery device according to claim 1, wherein a plurality of inclined ridges are arranged along an inner wall of the sleeve,
wherein the plurality of inclined ridges cooperate with a plurality of inclined surfaces of a plurality of protrusions provided by the rotatable cylindrical driver.

10. The delivery device of claim 1, wherein a plurality of inclined surfaces are provided on a rear end surface of the sleeve,
wherein the plurality of inclined surfaces co-act with a plurality of corresponding surfaces of a tubular part of the button.

11. The delivery device of claim 10, wherein the plurality of inclined surfaces provided on the rear end surface of the sleeve are arranged to co-act with the plurality of corresponding surfaces of a tubular part of the button, and
serve the purpose of holding the button in closed and open positions.

12. The delivery device of claim 11, wherein in the open position, the plurality of longitudinal ridges are aligned with a plurality of grooves of the button, thereby enabling the button to be pushed into the elongated body.

13. The delivery device of claim 10, wherein the plurality of inclined surfaces provided on the rear end surface of the sleeve and the plurality of corresponding surfaces of a tubular part of the button, serve the purpose of providing a tactile feedback to a user of the delivery device.

14. The delivery device according to claim 1, wherein the button further comprises a front cylindrical part provided inside the elongated body.

15. The delivery device according to claim 14, wherein the button is prevented from rearward movement by a circumferential ledge that is in contact with an inwardly directed ledge of the elongated body.

16. The delivery device of claim 1, wherein the button further comprises a front cylindrical part that is arranged with a plurality of longitudinal grooves arranged with a pitch and a width that corresponds to a plurality of longitudinal ridges provided on an inner surface of the elongated body.

17. The delivery device of claim 1, wherein a front end surface of the button is arranged with a plurality of inclined surfaces and stop ledges.

18. The delivery device of claim 1, wherein a perimeter surface of the button further comprises a release button, wherein the release button interacts with a respective through hole or indentation on a perimeter surface of the elongated body near the rear end of the elongated body.

19. The delivery device according to claim 1, wherein the button comprises a lockable button.

20. The delivery device according to claim 19, wherein the lockable button is unlocked by being turned until a plurality of stop ledges on a front end surface of the lockable button come into contact with a plurality of ridges provided by the elongated body.

21. The delivery device according to claim 19, wherein the lockable button is unlocked by pressing a release button whereby the lockable button is ejected towards its rear end and forced to turn until a plurality of stop ledges on a front surface come in contact with a plurality of ridges of the elongated body due to a pressure exerted by a spring.

22. The delivery device of claim 1 further comprising: a resilient member arranged between an inner surface of the button and the rear end of the rotatable cylindrical driver.

23. The delivery device of claim 1, further comprising a container arranged within the front end of the elongated body.

24. The delivery device of claim 1, wherein the plunger rod is rotatable relative to the elongated body.

* * * * *